United States Patent [19]

Huynh-Ba et al.

[11] Patent Number: 4,686,289
[45] Date of Patent: Aug. 11, 1987

[54] ANISOTROPIC COMPOUNDS AND LIQUID CRYSTAL MIXTURES

[75] Inventors: Tuong Huynh-Ba, Pully; Maged A. Osman, Zürich, both of Switzerland

[73] Assignee: Merck Patent Gesellschaft mit beschrankter Haftung, Darmstadt, Fed. Rep. of Germany

[21] Appl. No.: 832,801

[22] Filed: Feb. 25, 1986

Related U.S. Application Data

[63] Continuation-in-part of Ser. No. 648,439, Sep. 10, 1984, Pat. No. 4,622,163.

[30] Foreign Application Priority Data

Sep. 10, 1983 [DE]  Fed. Rep. of Germany ....... 3332691

[51] Int. Cl.$^4$ .................... C09K 10/30; C07D 403/12; C07C 121/46; C07C 19/00; C07C 21/66; C07C 69/76; C07C 43/225

[52] U.S. Cl. ............................. 544/224; 252/299.61; 252/299.62; 252/299.63; 544/238; 544/239; 558/388; 558/398; 558/406; 558/410; 558/389; 558/399; 558/409; 558/426; 558/428; 558/429; 558/430; 560/1; 560/55; 560/64; 560/66; 560/73; 560/105; 560/108; 560/116; 560/8; 560/59; 560/65; 560/72; 560/102; 560/107; 560/118; 560/126; 560/138; 560/141; 568/631; 568/632; 568/634; 568/642; 568/659; 568/661; 568/664; 568/665; 570/129; 570/130; 570/182; 570/183; 570/184; 570/185; 570/187; 570/188

[58] Field of Search ........... 252/299.5, 299.61, 299.62, 252/299.63; 350/350 R, 350 S; 558/388, 389, 398, 399, 406, 409, 410, 426, 428, 429, 430; 544/238, 224, 239; 560/1, 8, 55, 59, 64, 65, 66, 72, 73, 102, 105, 107, 108, 116, 118, 126, 138, 141; 568/632, 634, 631, 642, 659, 661, 664, 665; 570/129, 130, 183, 184, 185, 182, 187, 188

[56] References Cited

U.S. PATENT DOCUMENTS

| 3,365,505 | 1/1968 | Norell | 252/299.63 |
|---|---|---|---|
| 4,147,655 | 4/1979 | Dubois et al. | 252/299.67 |
| 4,393,258 | 7/1983 | Sato et al. | 252/299.63 |
| 4,400,293 | 8/1983 | Romer et al. | 252/499.63 |
| 4,419,263 | 12/1983 | Praeflke et al. | 252/299.63 |
| 4,431,853 | 2/1984 | Sato et al. | 252/299.63 |
| 4,439,015 | 3/1984 | Rich et al. | 252/299.63 |
| 4,480,117 | 10/1984 | Takatsu et al. | 252/299.63 |
| 4,510,069 | 4/1985 | Eidenschink et al. | 252/299.63 |
| 4,514,044 | 4/1985 | Gunjima et al. | 252/299.63 |
| 4,514,317 | 4/1985 | Huynh-Ba et al. | 252/299.63 |
| 4,556,745 | 12/1985 | Carr et al. | 252/299.62 |
| 4,558,151 | 12/1985 | Takatsu et al. | 252/299.63 |
| 4,583,826 | 4/1986 | Petrzilka et al. | 252/299.63 |
| 4,602,851 | 7/1986 | Jenner et al. | 252/299.63 |
| 4,606,845 | 8/1986 | Romer et al. | 252/299.63 |
| 4,610,805 | 9/1986 | Schellenberger et al. | 252/299.63 |
| 4,621,901 | 11/1986 | Petrzilka et al. | 252/299.63 |
| 4,622,163 | 11/1986 | Huynh-Ba et al. | 252/299.63 |
| 4,637,897 | 1/1987 | Kelly | 252/299.63 |

FOREIGN PATENT DOCUMENTS

| 107116 | 5/1984 | European Pat. Off. | 252/299.63 |
|---|---|---|---|
| 111695 | 6/1984 | European Pat. Off. | 252/299.61 |
| 107668 | 1/1985 | European Pat. Off. | 252/299.63 |
| 168043 | 1/1986 | European Pat. Off. | 252/299.63 |
| 3226051 | 2/1983 | Fed. Rep. of Germany | 252/299.63 |
| 3333677 | 4/1985 | Fed. Rep. of Germany | 252/299.63 |
| 56-81384 | 7/1981 | Japan | 252/299.6 |
| 60-84230 | 5/1985 | Japan | 252/299.63 |
| 2134110 | 8/1984 | United Kingdom | 252/299.63 |

OTHER PUBLICATIONS

Demus, D., et al., Flussige Kristalle in Tabellen II, Veb Deutscher Verlag fur Grundstoffinahstaie, Leipzig, pp. 99-103 (1984).

Osman, M., Z. Naturforsch, vol. 38c, pp. 693-697 (1983).

Osman, M. A., et al., Mol. Cayst. Liq. Cayst., vol. 82 (Letters), pp. 339-344 (1/1983).

Kelly, S. M., et al., Helvetica Chimica Acta, vol. 68, pp. 1444-1452 (1985).

Praefcke, K., et al., Chemiker-Zeitung, vol. 104, pp. 269-271, No. 9 (1980).

Primary Examiner—Teddy S. Gron
Attorney, Agent, or Firm—Millen & White

[57] ABSTRACT

New anisotropic compounds with a cross-polarizing substituent have the formula (1)

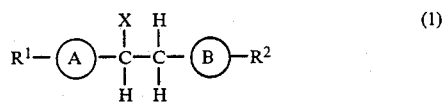

The increase in $\epsilon\perp$ is achieved by the polarizing group X, preferably the cyano group or a halogen atom, which is not laterally on the ring, as with the known compounds, but is on the bridge, that is to say is part of the main bridge bonding rings A and B to one another. Ring A has the formula (1a) or (1b) given herein and is always cycloaliphatic, while ring B can be identical to ring A or is an aromatic ring of the formula (1c) or (1d) herein. $R^1$ and $R^2$ are identical or different end groups of the formula (1e) herein.

The radical X on the bridge causes less widening of the molecule than a radical X on a ring, which provides comparatively higher clear points and moreover enables aromatic rings to be omitted from the anisotropic compounds.

17 Claims, No Drawings

ANISOTROPIC COMPOUNDS AND LIQUID CRYSTAL MIXTURES

This application is a continuation-in-part of U.S. application Ser. No. 648,439, filed Sept. 10, 1984, now U.S. Pat. No. 4,622,163.

BACKGROUND OF THE INVENTION

The invention relates to new anisotropic compounds which carry at least one cross-polarizing substituent and offer reduced viscosities and increased clear points; the invention furthermore relates to liquid crystal mixtures (LC mixtures) containing these compounds as components.

As is known, nematic LC mixtures with negative $\Delta\epsilon$ values are required for various types of electrooptical displays, for example for the so-called "guest/host displays" (GHD) and the homeotropic-nematic displays (HND), $\Delta\epsilon$ being designated DC anisotropy or DCA and being defined as $\Delta\epsilon = \epsilon'' - \epsilon\bot'$, wherein $\epsilon''$ is the dielectric constant (DC) parallel to the longitudinal axis of the molecule and $\epsilon\bot$ is the DC perpendicular to the molecular axis.

Furthermore, for certain types of operation of the displays, for example for multiplex operation, LC mixtures with an overall positive DCA but as small as possible a value of the ratio $$\frac{\Delta\epsilon}{\epsilon\bot}$$

are required, that is to say mixtures or compounds with a significant value for $\epsilon\bot$.

The values of $\epsilon''$ and $\epsilon\bot$ are determined by the degree of polarization of the molecule in the direction parallel and, respectively, perpendicular to the longitudinal axis of the molecule; for example, a highly polarizing substituent, such as the cyano group or a halogen atom, as an end group—also designated a longitudinally polarizing substituent below—increases the value of $\epsilon''$, while such a substituent in the "lateral" position, that is to say more or less at right angles to the longitudinal direction of the molecule, increases the value of $\epsilon\bot$; these lateral substituents are here designated "cross-polarizing" substituents.

However, the LC mixtures and their components must also fulfil a number of other characteristics, including, in particular, a high photochemical, general chemical, heat and electrochemical stability and as low as possible a viscosity and low optical anisotropy (low tendency towards double refraction) and clear points which are as high as possible.

According to the prior art, negative DCA values or higher $\epsilon\bot$ contributions are generally achieved by providing an aromatic cyclic radical, usually a benzene ring, with at least one cross-polarizing substituent.

The known compounds with negative DCA thus have, as the characteristic element, cores having the structure

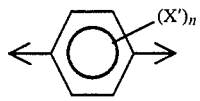

in which X' is the cross-polarizing group, for example cyano or halogen, n is 1 or 2 and the arrows approximately correspond to the longitudinal axis of the molecule. Such compounds are described, for example, in German Pat. Nos. A-2,240,864, 2,613,293, 2,835,662, 2,836,086, 2,835,728 and 2,937,770 and European Pat. No. A-0,023,728.

It is furthermore known, from European Patent Application No. 79,200,259.4, that at least one cross-polarizing substituent can be combined with a longitudinally polarizing substituent to obtain anisotropic compounds with positive DCA and small values of the ratio $$\frac{\Delta\epsilon}{\epsilon\bot}.$$

The known compounds have the common factor of widening of the molecule as a result of the cross-polarizing substituent or substituents, this being a disadvantage because it leads to a reduction in the clear point and frequently gives rise to a relatively high viscosity; since the lateral polarizing groups can in practice be introduced only into aromatic radicals, the necessity of the presence of an aromatic radical represents a further limitation.

SUMMARY OF THE INVENTION

Thus, it is an object of this invention to provide new anisotropic compounds which carry at least one cross-polarizing substituent but contain no cross-polarizing groups attached to cyclic radicals, so that the above disadvantages and limitations can be avoided.

Upon further study of the specification and appended claims, further objects and advantages of this invention will become apparent to those skilled in the art.

According to the invention, these objects have been achieved by providing new anisotropic compounds of the formula (1) which possess at least two cyclic radicals bonded to one another via a particular bridge member carrying the polarizing group (also designated the main bridge below):

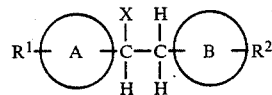

DETAILED DISCUSSION

The ring A is a cycloaliphatic ring of the formula (1a) or (1b)

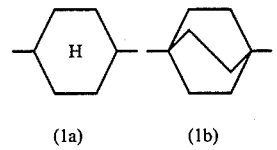

that is to say a trans-1,4-cyclohexyl radical or a 1,4-bicylco-(2,2,2)-octyl radical.

The ring B can also be a cycloaliphatic ring of the formula (1a) or (1b), or can be an aromatic radical of the formula (1c) or (1d)

(1c) [structure: phenyl ring]

(1d) [structure: pyridazine ring with N—N]

that is to say a 1,4-phenyl radical or a 3,6-pyridazinyl radical.

The polarizing group X, which is a halogen atom or the cyano group, must be attached to that C atom of the main bridge to which the cycloaliphatic radical, or one cycloaliphatic radical, is bonded directly. Since ring A must always be cycloaliphatic, while ring B can be cycloaliphatic or aromatic, this results in the position of X shown in formula (1). If ring B is also a cycloaliphatic radical, X could also be attached to the C atom of the main bridge bonded directly to ring B.

The groups $R^1$ and $R^2$ in formula (1) are identical or different end groups of the formula (1e)

$$R^3 + \bigcirc{C} Z \bigg]_{\overline{m}} \qquad (1e)$$

in which the ring C has one of the meanings given for ring B, that is to say is a radical of the formula (1a), (1b), (1c) or (1d), and thus can also be cycloaliphatic or aromatic; however, ring C in formula (1e) is optional, that is to say m is 0 or 1.

The bridge Z in formula (1e) is the covalent bond or a secondary bridge group of the formula —$CH_2O$—, —$C(X^1)(H)$—$CH_2$— or —COO—, wherein $X^1$ is hydrogen or has one of the meanings given for X, and in particular in each case also in reverse sequence, the provisos (a) and (b) described below, however, also being taken into consideration.

If $X^1$ in the secondary bridge has one of the meanings given for X, additional lateral polarization can be effected. For many purposes, Z is preferably in the form of a covalent bond.

$R^3$ can be hydrogen, if m is 1 and ring C is a cyclic radical of the formula (1c) or (1d), or, generally, is alkyl ($H_{2n+1}C_n$—), alkoxy ($H_{2n+1}C_n$—O—), alkoxycarbonyl ($H_{2n+1}C_n$—OC(O)—) or alkylcarbonyloxy groups ($H_{2n+1}C_n$—C(O)—O—), the alkyl part of which contains 1–12 C atoms (n=1–12) in a straight or branched, optionally chiral chain. Examples of the alkyl parts of the groups mentioned are thus methyl, ethyl, propyl, butyl, pentyl, hexy, heptyl, octyl, nonyl, decyl, undecyl and dodecyl groups, including the isomeric and chiral-isomeric alkyl groups, such as 2-methylbutyl, 2-methylbutoxy, 2-methylpentyl, 3-methylheptyl and the like. These alkyl parts preferably have a straight chain and 3–7 C atoms.

The alkyl parts of $R^3$ can carry one or more substituents, in particular halogen atoms or cyano groups, in each case at most one such substituent being attached to in each case one C atom of the alkyl part. The alkyl parts of $R^3$ preferably contain one or at most two such substituents, and in particular preferably on those C atoms of the alkyl part which are not too far removed from the associated ring, for example which are attached to atoms in the 1-, 2- or 3-position of the end group chain, if the atom (C or O) bonded to the associated ring is designated the atom in the 1-position of the chain. Under certain circumstances, especially if the substituent is cyano, the contribution to the longitudinal or cross-polarization can be increased by attaching the substituent to an even-numbered or odd-numbered atom of the chain of the end group.

Furthermore, fluorine, chlorine or cyano is in most cases preferred as the substituent of the alkyl part of $R^3$.

The actual conformation of the main bridge of the formula (1) corresponds to the equation $$R^1 - \bigcirc{A} - \overset{X}{\underset{}{C}} - \bigcirc{B} - R^2$$

and shows that the widening of the molecule caused by the laterally polarizing radical X on the bridge is lower in the anisotropic compounds according to the invention than in the known anisotropic compounds with X on the ring.

Concrete comparison values for the surprising improvements in the properties of compounds (1) according to the invention with laterally polarizing groups on the bridge as against comparable (in respect of DCA) compounds with laterally polarizing groups on the ring are given below in Example 2.

It is furthermore surprising that compounds with the stability required for LC mixtures are obtainable at all with highly polarizing groups on the bridge. Known compounds with cyano groups on the bridge have almost always proved to be unstable, and investigations by the Applicant Company have shown, that, for example, compounds with the "cyanobenzyl structure"

$$-\bigcirc{D}-\overset{CN}{\underset{H}{C}}-$$

in which D is an aromatic ring, like compounds with the "benzyl ether structure"

$$-\bigcirc{D}-\overset{H}{\underset{H}{C}}-O-$$

here do not give compounds with an adequate stability.

The following provisos or restrictions thus apply to compounds of the formula (1) according to the invention:

(a) groups of the formulae $$-\overset{H}{\underset{H}{C}}-O- \quad \text{and} \quad -\overset{X}{\underset{H}{C}}-$$

are not bonded directly via their C atoms to any aromatic radical of the formula (1c) or (1d), except for when X=F, and (b) $R^3$ in formula (1e) is not hydrogen if m is 0.

Preferred groups of compounds of the formula (1) according to the invention have the following features, individually or in combination:

X is the cyano group;

if X is halogen, fluorine and chlorine are preferred;

if R³ contains a substituted alkyl part, this preferably carries one or two substituents, preferred halogen atoms being fluorine and chlorine;

the molecule of the formula (1) preferably contains not more than one carboxyl group in total;

the molecule of the formula (1) preferably contains not more than one aromatic ring of the formula (1c) or (1d);

the molecule of the formula (1) preferably contains not more than three cyclic radicals in total;

the molecule of the formula (1) contains two or three cycloaliphatic radicals of the formula (1a) and/or (1b);

the molcule of the formula (1) contains two end groups with alkyl parts, each of which has 3-9 C atoms;

the substituent or substituents (at most two) of the alkyl parts of R³ are attached to those C atoms of the alkyl chain which are separated from the associated ring, that is to say the next ring, by not more than 2 atoms.

Compounds of the following formulae 2-5 are also preferred for many intended uses:

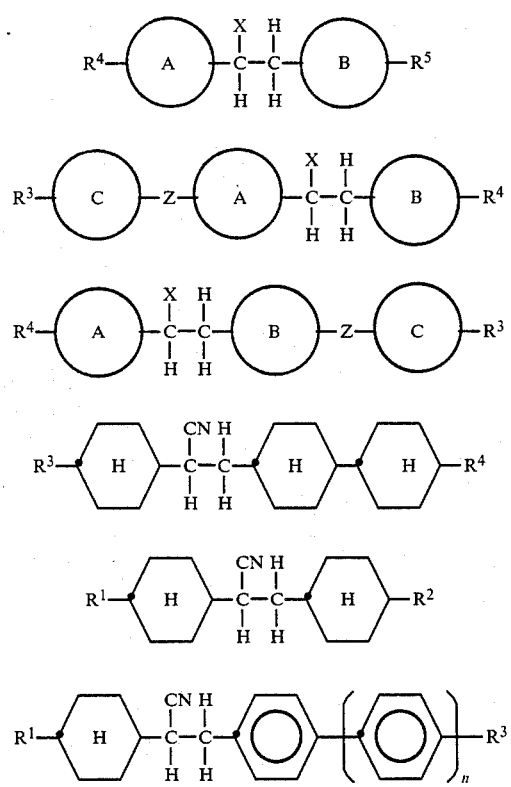

in which A, B, C, X, Z, R¹, R² and R³ have the abovementioned meaning, R⁴ and R⁵ have one of the meanings given for R³, and n is 0 or 1, with the exception of hydrogen; however, the invention is not limited to binuclear or trinuclear compounds (1), since both R¹ and R² can be identical or different groups of the formula (1e). Preferably, the compound of formula (5) has R³ and R⁴ groups both of which are $C_{1-12}$-alkyl groups, e.g., n-pentyl. Preferably, the compound of formula (6) has a $C_1$-$C_{12}$-alkyl radical as R¹ group and

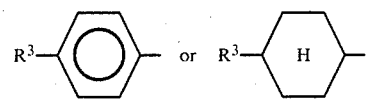

as R² group.

The invention furthermore relates to liquid crystal mixtures which contain at least one compound of the formula (1), for example in amounts of 1-30% by weight, it also being possible for the mixture to contain several different compounds of the formula (1), for example in a total amount of 5-70% by weight, preferably 15-65% by weight. As further components, the LC mixtures according to the invention can contain known anisotropic compounds and the additives appropriate for the intended use, such as dyestuffs, in particular pleochroic dyestuffs, optically active or cholesteric components and the like. The preparation, compositions and use of the mixtures and electro-optical cells of this invention are fully conventional as described, e.g., in U.S. Pat. Nos. 3,995,941; 3,951,846 and 4,285,829.

The new compounds of the formula (1) can be obtained by various processes which are known per se; the compounds (1) in which X in the main bridge is the cyano group can be obtained, for example, directly by condensation according to the following equation I:

Equation I

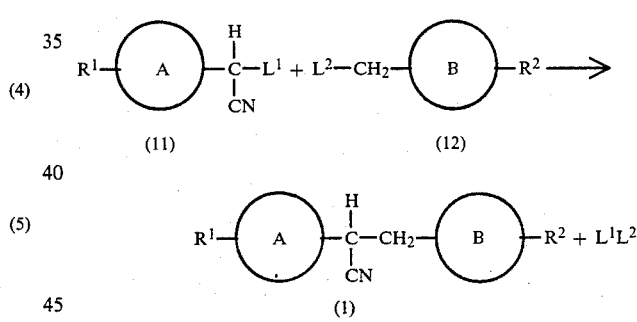

wherein R¹, R², A and B have the abovementioned meaning and L¹ and L² are leaving groups, such as, for example, L¹=H, L²=Br and the like. The condensation reaction is preferably carried out here in a liquid medium at elevated temperature in the presence of substances which accelerates the condensation, such as, for example, metallic sodium, or which bond the compound L¹L² formed as the by-product.

Suitable starting compounds of the formulae (11) and (12) are either known or are obtainable in accordance with the following equation II:

Equation II

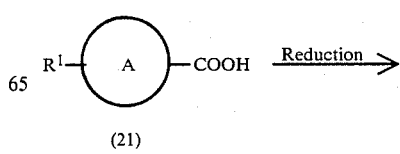

-continued

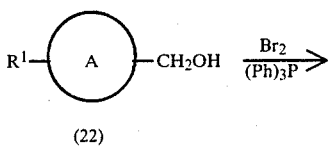

(22)

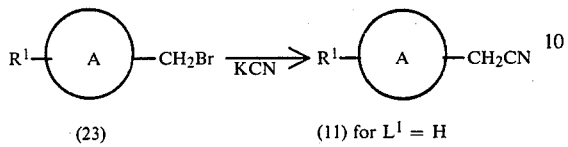

(23)   (11) for L¹ = H

Suitable starting compounds (21) for the synthesis according to equation II are known, or they can be obtained in a similar manner to the known compounds.

The reduction can be carried out in a manner which is known per se, for example with lithium aluminum hydride; the bromination is usually advantageously carried out with elemental bromine in the presence of triphenylphosphine, and the reaction with KCN can be achieved as described in Org. Synth. Coll. volume 3, 852 (1955).

The starting compounds (12) corresponding to the compounds (23)

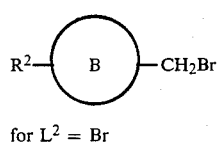

(12)

for L² = Br can also be obtained in an analogous manner according to equation II for the synthesis according to equation I, where B is an aromatic radical of the formula (1c) or (1d) and R¹=R², by using the corresponding carboxylic acids of the formula (210)

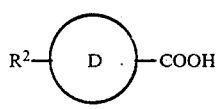

(210)

in which the ring D is a radical of the formula (1c) or (1d), instead of the compounds (21).

The following compounds are general examples of suitable compounds of the formulae (21) and (210):

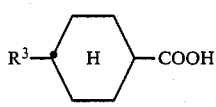

(21/1)

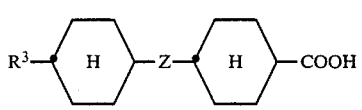

(21/2)

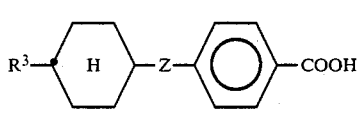

(210/1)

-continued

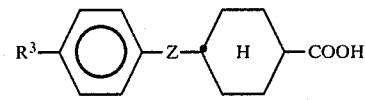

(21/3)

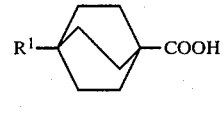

(21/4)

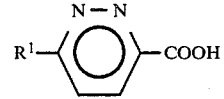

(210/2)

in which R¹ and R³ have the abovementioned meaning. The preparation of acids of the formula (21/4) is described, for example, in Mol. Cryst. Liqu. Cryst. 75 (1981) 95. The acids of the formula (210/2) can be obtained from the chloro- or bromo-pyridazine derivatives described in Z. für Chemie, 17 (1977) 333, using $CO_2$/Mg (Grignard).

The compounds of the formula (1) in which X in the main bridge is halogen can be obtained in accordance with the following equation III:

Equation III

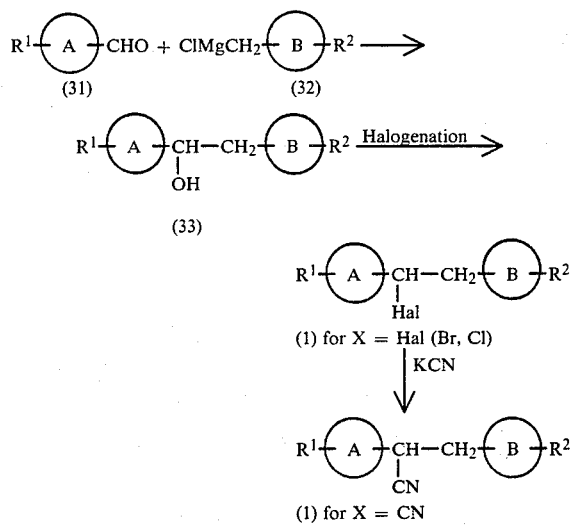

The reaction of (31) with (32) is a Grignard synthesis which is known per se, and the halogenation of (33) can be achieved with thionyl chloride or a phosphorous halide.

The corresponding compounds (1) for Hal=F or I can be obtained by trans-halogenation methods which are known per se, for example, in accordance with the method of Finkelstein, from the products of the synthesis according to equation III. The methods described by Gerstenberger et al in Angew. Chemie 93 (1981) 659 are usually also suitable for introducing fluorine by trans-halogenation.

Suitable starting compounds of the formula (31) and (32) are again either known or they can be obtained in a similar manner to the known compounds.

A further process for the preparation of compounds of the formula (1) comprises modifying the compounds (1) obtained in accordance with equation I or III, for example on the end groups $R^1$ and $R^2$, or by treating the compounds in which X in the main bridge is halogen, such as bromine, with potassium cyanide.

It is furthermore possible to use, instead of the starting compounds of the formulae (11), (12), (31) and (32) given in equations I and III, the corresponding precursors containing suitable reactive groups, for example halogen atoms, hydroxyl groups, carboxyl groups or the like, instead of the end groups $R^1$ and $R^2$, and then to convert these into the desired groups $R^1$ and $R^2$ by methods which are known per se when the synthesis routes of I or III have ended.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention. In all preparation methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of 1,2-bis-(4-trans-pentylcyclohexyl)-1-cyanoethane (formula (2), $R^4=R^5=$-n-pentyl, X=CN, A=B=(1a))

0.5 g of metallic sodium was suspended in a solution of 1.93 g (0.01 mole) of 4-trans-cyanomethyl-1-pentylcyclohexane in 10 ml of benzene. The suspension was heated at the reflux temperature for 60 minutes. 2.02 g (0.01 mole) of 4-trans-bromomethyl-1-pentylcyclohexane were then added dropwise, with stirring.

When the reaction had ended, the reaction mixture was poured onto dilute cold hydrochloric acid and the resulting mixture was extracted with dimethyl ether. The crude target product was purified by chromatography over silica gel. Melting point 41.3° C., clear point 61.5° C. $\Delta\epsilon=4.3$.

The following compounds are prepared analogously:
1,2-bis-(4-trans-butylcyclohexyl)-1-cyanoethane
1,2-bis-(4-trans-propylcyclohexyl)-1-cyanoethane, melting point 43°, clear point 36°
1,2-bis-(4-trans-hexylcyclohexyl)-1-cyanoethane,
1,2-bis-(4-trans-heptylcyclohexyl)-1-cyanoethane,
1-(4-trans-pentylcyclohexyl)-2-(4-trans-propylcyclohexyl)-1-cyanoethane, melting point 45°, clear point 47°
1-(4-trans-pentylcyclohexyl)-2-(4-propylphenyl)-1-cyanoethane
1-(4-trans-pentylcyclohexyl)-2-(4-butylphenyl)cyanoethane
1-(4-trans-pentycyclohexyl)-2-(4-pentylphenyl)cyanoethane
1-(4-trans-pentylcyclohexyl)-2-(4-hexylphenyl)cyanoethane
1-(4-trans-pentylcyclohexyl)-2-(4-heptylphenyl)-cyanoethane
1-(4-trans-pentylcyclohexyl)-2-(4-octylphenyl)cyanoethane
1-(4-trans-pentylcyclohexyl)-2-(4-butoxyphenyl)-cyanoethane
1-(4-trans-pentylcyclohexyl)-2-(4-pentoxyphenyl)-cyanoethane
1-(4-trans-pentylcyclohexyl)-2-(4-hexoxyphenyl)-cyanoethane
1-(4-trans-pentylcyclohexyl)-2-(4-heptoxyphenyl)-cyanoethane
1-(4-trans-pentylcyclohexyl)-2-(4-octoxyphenyl)-cyanoethane
1-(4-trans-butylcyclohexyl)-2-(4-propylphenyl)cyanoethane
1-(4-trans-butylcyclohexyl)-2-(4-butylphenyl)cyanoethane
1-(4-trans-butylcyclohexyl)-2-(4-pentylphenyl)cyanoethane
1-(4-trans-butylcyclohexyl)-2-(4-hexylphenyl)cyanoethane
1-(4-trans-butylcyclohexyl)-2-(4-heptylphenyl)cyanoethane
1-(4-trans-butylcyclohexyl)-2-(4-octylphenyl)cyanoethane
1-(4-trans-butylcyclohexyl)-2-(4-butoxyphenyl)cyanoethane
1-(4-trans-butylcyclohexyl)-2-(4-pentoxyphenyl)-cyanoethane
1-(4-trans-butylcyclohexyl)-2-(4-hexoxyphenyl)cyanoethane
1-(4-trans-butylcyclohexyl)-2-(4-heptoxyphenyl)-cyanoethane
1-(4trans-butylcyclohexyl)-2-(4-octoxyphenyl)cyanoethane
1-(4-trans-propylcyclohexyl)-2-(4-propylphenyl)-cyanoethane
1-(4-trans-propylcyclohexyl)-2-(4-butylphenyl)-cyanoethane
1-(4-trans-propylcyclohexyl)-2-(4-pentylphenyl)-cyanoethane
1-(4-trans-propylcyclohexyl)-2-(4-hexylphenyl)cyanoethane
1-(4-trans-propylcyclohexyl)-2-(4-heptylphenyl)-cyanoethane
1-(4-trans-propylcyclohexyl)-2-(4-octylphenyl)cyanoethane
1-(4-trans-propylcyclohexyl)-2-(4-butoxyphenyl)-cyanoethane
1-(4-trans-propylcyclohexyl)-2-(4-pentoxyphenyl)-cyanoethane
1-(4-trans-propylcyclohexyl)-2-(4-hexoxyphenyl)-cyanoethane
1-(4-trans-propylcyclohexyl)-2-(4-heptoxyphenyl)-cyanoethane
1-(4-trans-propylcyclohexyl)-2-(4-octoxyphenyl)-cyanoethane
1-(4-trans-pentylcyclohexyl)-2-[4-trans(p-propylphenyl)cyclohexyl]-cyanoethane
1-(4-trans-pentylcyclohexyl)-2-[4-trans(p-butylphenyl)-cyclohexyl]-cyanoethane 1-(4-trans-pentylcyclohexyl)-2-[4-trans(p-pentyl-phenyl)cyclohexyl]-cyanoethane
1-(4-trans-pentylcyclohexyl)-2-[4-trans(p-hexylphenyl)-cyclohexyl]-cyanoethane
1-(4-trans-pentylcyclohexyl)-2-[4-trans(p-heptyl-phenyl)cyclohexyl]-cyanoethane
1-(4-trans-pentylcyclohexyl)-2-[4-trans(p-octylphenyl)-cyclohexyl]-cyanoethane
1-(4-trans-pentylcyclohexyl)-2-[4-trans(p-butoxy-phenyl)cyclohexyl]-cyanoethane
1-(4-trans-pentylcyclohexyl)-2-[4-trans(p-pentoxy-phenyl)cyclohexyl]-cyanoethane
1-(4-trans-pentylcyclohexyl)-2-[4-trans(p-hexoxy-phenyl)cyclohexyl]-cyanoethane
1-(4-trans-pentylcyclohexyl)-2-[4-trans(p-heptoxy-phenyl)cyclohexyl]-cyanoethane
1-(4-trans-pentylcyclohexyl)-2-[4-trans(p-octoxy-phenyl)cyclohexyl]-cyanoethane
1-(4-trans-butylcyclohexyl)-2-[4-trans(p-propylphenyl)-cyclohexyl]-cyanoethane
1-(4-trans-butylcyclohexyl)-2-[4-trans(p-butylphenyl)-cyclohexyl]-cyanoethane
1-(4-trans-butylcyclohexyl)-2-[4-trans(p-phenylphenyl)-cyclohexyl]-cyanoethane
1-(4-trans-butylcyclohexyl)-2-[4-trans(p-hexylphenyl)-cyclohexyl]-cyanoethane
1-(4-trans-butylcyclohexyl)-2-[4-trans(p-heptylphenyl)-cyclohexyl]-cyanoethane
1-(4-trans-butylcyclohexyl)-2-[4-trans(p-octylphenyl)-cyclohexyl]-cyanoethane
1-(4-trans-butylcyclohexyl)-2-[4-trans(p-butoxy-phenyl)cyclohexyl]-cyanoethane
1-(4-trans-butylcyclohexyl)-2-[4-trans(p-pentoxy-phenyl)cyclohexyl]-cyanoethane
1-(4-trans-butylcyclohexyl)-2-[4-trans(p-hexoxy-phenyl)cyclohexyxl]-cyanoethane
1-(4trans-butylcyclohexyl)-2-[4-trans(p-heptoxy-phenyl)cyclohexyl]-cyanoethane
1-(4-trans-butylcyclohexyl)-2-[4-trans(p-octoyphenyl)-cyclohexyl]-cyanoethane
1-(4-trans-propylcyclohexyl)-2-[4-trans(p-propyl-phenyl)cyclohexyl]-cyanoethane
1-(4-trans-propylcyclohexyl)-2-[4-trans(p-butylphenyl)-cyclohexyl]-cyanoethane
1-(4-trans-propylcyclohexyl)-2-[4-trans(p-pentyl-phenyl)cyclohexyl]-cyanoethane
1-(4-trans-propylcyclohexyl)-2-[4-trans(p-hexyl-phenyl)cyclohexyl]-cyanoethane
1-(4-trans-propylcyclohexyl)-2-[4-trans(p-heptyl-phenyl)cyclohexyl]-cyanoethane
1-(4-trans-propylcyclohexyl)-2-[4-trans(p-octylphenyl)-cyclohexyl]-cyanoethane
1-(4-trans-propylcyclohexyl)-2-[4-trans(p-butoxy-phenyl)cyclohexyl]-cyanoethane
(4-trans-propylcyclohexyl)-2-[4-trans(p-pentoxy-phenyl)cyclohexyl]-cyanoethane
1-(4-trans-propylcyclohexyl)-2-[4-trans(p-hexoxy-phenyl)cyclohexyl-cyanoethane
1-(4-trans-propylcyclohexyl)-2-[4-trans(p-heptoxy-phenyl)cyclohexyl]-cyanoethane
1-(4-transpropylcyclohexyl)-2-[4-trans(p-octoxyheptox-yphenyl)cyclohexyl]-cyanoethane
1-(4-trans-pentylcyclohexyl)-2-(4'-propylbiphenyl)-1-cyanoethane
1-(4-trans-pentylcyclohexyl)-2-(4'-butylbiphenyl)-1-cyanoethane
1-(4-trans-pentylcyclohexyl)-2-(4'-pentylbiphenyl)-1-cyanoethane
1-(4-trans-pentylcyclohexyl)-2-(4'-hexylbiphenyl)-1-cyanoethane
1-(4-trans-pentylcyclohexyl)-2-(4'-heptylbiphenyl)-1-cyanoethane
1-(4-trans-pentylcyclohexyl)-2-(4'-octylbiphenyl)-1-cyanoethane
1-(4-trans-pentylcyclohexyl)-2-(4'-butopxybiphenyl)-1-cyanoethane
1-(4-trans-pentylcyclohexyl)-2-(4'-pentoxybiphenyl)-1-cyanoethane
1-(4-trans-pentylcyclohexyl)-2-(4'-hexoxybiphenyl)-1-cyanoethane
1-(4-trans-pentylcyclohexyl)-2-(4'-heptoxybiphenyl)-1-cyanoethane
1-(4-trans-pentylcyclohexyl)-2-(4'-octoxybiphenyl)-1-cyanoethane
1-(4-trans-propylcyclohexyl)-2-(4'-propylphenyl)-1-cyanoethane
1-(4-trans-propylcyclohexyl)-2-(4'-butylphenyl)-1-cyanoethane
1-(4-trans-propylcyclohexyl)-2-(4'-pentylphenyl)-1-cyanoethane
1-(4-trans-propylcyclohexyl)-2-(4'-hexylphenyl)-1-cyanoethane
1-(4-trans-propylcyclohexyl)-2-(4'-heptylphenyl)-1-cyanoethane
1-(4-trans-propylcyclohexyl)-2-(4'-octylphenyl)-1-cyanoethane
1-(4-trans-propylcyclohexyl)-2-(4'-butoxyphenyl)-1-cyanoethane
1-(4-trans-propylcyclohexyl)-2-(4'-pentoxyphenyl)-1-cyanoethane
1-(4-trans-propylcyclohexyl)-2-(4'-hexoxyphenyl)-1-cyanoethane
1-(4-trans-propylcyclohexyl)-2-(4'-heptoxyphenyl)-1-cyanoethane
1-(4-trans-propylcyclohexyl)-2-(4'-octoxyphenyl)-1-cyanoethane
1-(4-trans-heptylcyclohexyl)-2-(4'-propylphenyl)-1-cyanoethane
1-(4-trans-heptylcyclohexyl)-2-(4'-butylphenyl)-1-cyanoethane
1-(4-trans-heptylcyclohexyl)-2-(4'-pentylphenyl)-1-cyanoethane
1-(4-trans-heptylcyclohexyl)-2-(4'-hexylphenyl)-1-cyanoethane
1-(4-trans-heptylcyclohexyl)-2-(4'-heptylphenyl)-1-cyanoethane
1-(4-trans-heptylcyclohexyl)-2-(4'-octylphenyl)-1-cyanoethane
1-(4-trans-hepylcyclohexyl)-2-(4'-butoxyphenyl)-1-cyanoethane
1-(4-transl-heptylcyclohexyl)-2-(4'-pentoxyphenyl)-1-cyanoethane
1-(4-trans-heptylcyclohexyl)-2-(4'-hexoyphenyl)-1-cyanoethane
1-(4-trans-heptylcyclohexyl)-2-(4'-heptoxyphenyl)-1-cyanoethane
1-(4-trans-heptylcyclohexyl)-2-(4'-octoxyphenyl)-1-cyanoethane

EXAMPLE 2

Preparation of 1-(4'-trans-pentyl-4-trans-bicyclohexyl)-2-(4-trans-pentylcyclohexyl)-2-cyanoethane (formula (5), $R^3 = R^4 =$ n-pentyl).

0.5 g of sodium was added to 1.93 g (0.01 mole) of 4-trans-cyanomethyl-1-pentylcyclohexane in 10 ml of benzene and the mixture was heated at the reflux temperature for 60 minutes, with vigorous stirring.

0.01 Mole of 4-trans-bromomethyl-1-(4'-trans-pentylcyclohexyl)-cyclohexane was added to the resulting dispersion, with stirring, and the mixture was heated until the reaction had ended. The reaction mixture was poured onto a HCl/ice mixture. The crude product was extracted from the resulting mixture with dimethyl ether and was chromatographed over silica gel for purification. Melting point 71.5° C., clear point 173° C., $\Delta\epsilon = -3.6$, $\Delta\eta = 0.06$.

The compound of the formula (V)

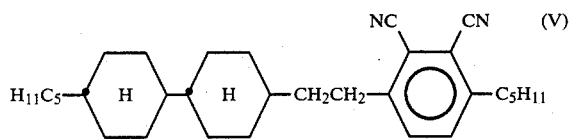

which is not according to the invention, was used for comparison with the target compound according to the invention prepared in this example, because this comparison compound has approximately the same negative DCA as the compound of Example 2, although it requires two cyano groups on the ring to achieve this. This comparison shows the surprising advantages of compounds (1) according to the invention with a laterally polarizing group on the bridge as opposed to the prior art in two respects: on the one hand, according to the invention, a DCA which is virtually just as negative can already be achieved with a single cyano group, but on the bridge, as is achieved with two lateral cyano groups on the ring; this is probably to be attributed to the fact that the cyano group on the bridge causes virtually no polarisation moment in the direction of the longitudinal axis of the molecule, while the cyano groups on the ring cause polarization moments in this direction which are considerable but cancel each other out.

On the other hand, the compound according to the invention has a very broad mesophase (71.5° to 173° C.), while the comparison compound has a melting point of 163° C. and has no mesophase at all.

The following compounds are prepared analogously:
1-(4'-trans-propyl-4-trans-bicyclohexyl)-2-(4-trans-propylcyclohexyl)-2-cyanoethane
1-(4'-trans-propyl-4-trans-bicyclohexyl)-2-(4-trans-butylcyclohexyl)-2-cyanoethane
1-(4'-trans-propyl-4-trans-bicyclohexyl)-2-(4-trans-pentylcyclohexyl)-2-cyanoethane
1-(4'-trans-propyl-4-trans-bicyclohexyl)-2-(4-trans-hexylcyclohexyl)-2-cyanoethane
1-(4'-trans-propyl-4-trans-bicyclohexyl)-2-(4-trans-heptylcyclohexyl)-2-cyanoethane
1-(4'-trans-butyl-4-trans-bicyclohexyl)-2-(4-trans-propylcyclohexyl)-2-cyanoethane
1-(4'-trans-butyl-4-trans-bicyclohexyl)-2-(4-trans-butylcyclohexyl)-2-cyanoethane
1-(4'-trans-butyl-4-trans-bicyclohexyl)-2-(4-trans-pentylcyclohexyl)-2-cyanoethane
1-(4'-trans-butyl-4-trans-bicyclohexyl)-2-(4-trans-hexylcyclohexyl)-2-cyanoethane
1-(4'-trans-butyl-4-trans-bicyclohexyl)-2-(4-trans-heptylcyclohexyl)-2-cyanoethane
1-(4'-trans-pentyl-4-trans-bicyclohexyl)-2-(4-trans-propylcyclohexyl)-2-cyanoethane, melting point 66°, clear point 165°
1-(4'-trans-pentyl-4-trans-bicyclohexyl)-2-(4-trans-butylcyclohexyl)-2-cyanoethane
1-(4'-trans-pentyl-4-trans-bicyclohexyl)-2-(4-trans-hexyl)cyclohexyl)-2-cyanoethane
1-(4'-trans-pentyl-4-trans-bicyclohexyl)-2-(4-trans-heptyl)cyclohexyl)-2-cyanoethane
1-(4'-trans-heptyl-4-trans-bicyclohexyl)-2-(4-trans-propylcyclohexyl)-2-cyanoethane
1-(4'-trans-heptyl-4-trans-bicyclohexyl)-2-(4-trans-butylcyclohexyl)-2-cyanoethane
1-(4'-trans-heptyl-4-trans-bicyclohexyl)-2-(4-trans-pentylcyclohexyl)-2-cyanoethane
1-(4'-trans-heptyl-4-trans-bicyclohexyl)-2-(4-trans-hexylcyclohexyl)-2-cyanoethane
1-(4'-trans-heptyl-4-trans-bicyclohexyl)-2-(4-trans-heptylcyclohexyl)-2-cyanoethane
1-(4'-trans-hexylcyclohexyl)-2-(4'-trans-propyl-4-trans-bicyclohexyl)-2-cyanoethane
1-(4'-trans-hexylcyclohexyl)-2-(4'-trans-butyl-4-trans-bicyclohexyl)-2-cyanoethane
1-(4'-trans-hexylcyclohexyl)-2-(4'-trans-pentyl-4-trans-bicyclohexyl)-2-cyanoethane
1-(4'-trans-hexylcyclohexyl)-2-(4'-trans-hexyl-4-trans-bicyclohexyl)-2-cyanoethane
1-(4'-trans-hexylcyclohexyl)-2-(4'-trans-heptyl-4-trans-bicyclohexyl)-2-cyanoethane
1-(4'-trans-propylcyclohexyl)-2-(4'-trans-propyl-4-trans-bicyclohexyl)-2-cyanoethane
1-(4'-trans-propylcyclohexyl)-2-(4'-trans-butyl-4-trans-bicyclohexyl)-2-cyanoethane
1-(4'-trans-propylcyclohexyl)-2-(4'-trans-bicyclohexyl)-2-cyanoethane, melting point 70°, clear point 167°
1-(4'-trans-propylcyclohexyl)-2-(4'-trans-hexyl-4-trans-bicyclohexyl)-2-cyanoethane
1-(4'-trans-propylcyclohexyl)-2-(4'-trans-heptyl-4-trans-bicyclohexyl)-2-cyanoethane
1-(4'-trans-pentylcyclohexyl)-2-(4'-trans-pentyl-4-trans-bicyclohexyl)-2-cyanoethane, melting point 60°, clear point 171°
1,2-(4α-trans-pentyl-4-trans-bicyclohexyl)-2-cyanoethane, melting point 123°, clear point 284°
1,2-bis-(4'-trans-butyl-4-trans-bicyclohexyl)-2-cyanoethane
1,2-bis-(4'-trans-propyl-4-trans-bicyclohecyl)-2-cyanoethane

EXAMPLE 3

Preparation of 1,2-bis-(4-trans-propylcyclohexyl)-1-cyanoethane (formula (2), $R^4 = R^5 =$ n-propyl, X=Cn, A=B=(1a))

The target product was obtained by the process described in Example 1, by reacting 4-trans-cyanomethyl-1-propylcyclohexane with 4-trans-bromomethyl-1-propylcyclohexane; melting point 45.7° C., clear point (37.0)°C.

Further examples of compounds according to the invention are mentioned below:
1,2-bis-(4-trans-propylcyclohexyl)-1-fluoro-ethane
1,2-bis-(4-trans-propylcyclohexyl)-1-chloro-ethane
1,2-bis-(4-trans-propylcyclohexyl)-1-bromo-ethane 1,2-bis-(4-trans-propylcyclohexyl)-1-cyano-ethane
1,2-bis-(4-trans-fluoropropylcyclohexyl)-1-cyano-ethane
1,2-bis-(4-trans-propyloxycarbonylcyclohexyl)-1-fluoro-ethane
1,2-bis-(4-trans-propyloxycarbonylcyclohexyl)-1-chloro-ethane
1,2-bis-(4-trans-propyloxycarbonylcyclohexyl)-1-bromo-ethane
1,2-bis-(4-trans-propyloxycarbonylcyclohexyl)-1-cyano-ethane
1,2-bis-(4-trans-fluoropropyloxycarbonylcyclohexyl)-1-cyano-ethane
1-(4'-trans-propyl-4-trans-bicyclohexyl)-2-(4trans-propylcyclohexyl)-2-fluoro-ethane
1-(4'-trans-propyl-4-trans-bicyclohexyl)-2-(4-trans-propylcyclohexyl)-2-chloro-ethane
1-(4'-trans-propyl-4-trans-bicyclohexyl)-2-(4-trans-propylcyclohexyl)-2-bromo-ethane
1-(4'-trans-propyl-4-trans-bicyclohexyl)-2-(4-trans-propyloxycarbonylcyclohexyl)-2-fluoro-ethane
1-(4'-trans-propyl-4-trans-bicyclohexyl)-2-(4-trans-propyloxycarbonylcyclohexyl)-2-chloro-ethane
1-(4'-trans-propyl-4-trans-bicyclohexyl)-2-(4-trans-propyloxycarbonylcyclohexyl)-2-bromo-ethane
1-(4'-trans-propyl-4-trans-bicyclohexyl)-2-(4-trans-propyloxycarbonylcyclohexyl)-2-cyano-ethane
1-(4-trans(2-(4-trans-propylcyclohexyl)-ethyl)-cyclohexyl)-2-(4-trans-propylcyclohexyl)-2-fluoro-ethane
1-(4-trans-(2-(4-trans-propylcyclohexyl)-ethyl)-cyclohexyl)-2-(4-trans-propylcyclohexyl)-2-chloro-ethane
1-(4-trans-(2-(4-trans-propylcyclohexyl)-ethyl)-cyclohexyl)-2-(4-trans-propylcyclohexyl)-2-bromo-ethane
1-(4-trans-(2-(4-trans-propylcyclohexyl)-ethyl)-cyclohexyl)-2-(4-trans-propylcyclohexyl)-2-cyano-ethane
1-(4-trans-(2-(4-trans-propylcyclohexyl)-1-fluoroethyl)-cyclohexyl)-2-(4-trans-propylcyclohexyl)-2-fluoro-ethane
1-(4-trans-(2-(4-trans-propylcyclohexyl)-1-fluoroethyl)-cyclohexyl)-2-(4-trans-propylcyclohexyl)-2-cyano-ethane
1-(4-trans-(2-(4-trans-propylcyclohexyl)-1-cyanoethyl)-cyclohexyl)-2-(4-trans-propylcyclohexyl)-2-fluoro-ethane
1-(4-trans-(2-(4-trans-propylcyclohexyl)-1-cyanoethyl)-cyclohexyl)-2-(4-trans-propylcyclohexyl)-2-cyano-ethane
1-(4-propyl-1-bicyclo-(2,2,2)-octyl)-2-(4-trans-propylcyclohexyl)-1-fluoro-ethane
1-(4-1-bicyclo-(2,2,2)-octyl)-2-(4-trans-propylcyclohexyl)-1-chloro-ethane
1-(4-propyl-1-bicyclo-(2,2,2)-octyl)-2-(4-trans-propylcyclohexyl)-1-bromo-ethane
1-(4-propyl-1-bicyclo-(2,2,2)-octyl)-2-(4-trans-propylcyclohexyl)-1-cyano-ethane
1-(4-propyl-1-bicyclo-(2,2,2)-octyl)-2-(4-trans-propyloxycarbonylcyclohexyl)-1-fluoro-ethane
1-(4-propyl--bicyclo-(2,2,2)-octyl)-2-(4-trans-propyloxycarbonylcyclohxyl)-1-cyano-ethane
1-(4-trans-propylcyclohexyl)-2-(4-pentylphenyl)-1-fluoro-ethane
1-(4-trans-propylcyclohexyl)-2-(4-pentylphenyl)-1-chloro-ethane
1-(4-trans-propylcyclohexyl)-2-(4-pentylphenyl)-1-bromo-ethane
1-(4-trans-propylcyclohexyl)-2-(4-pentylphenyl)-1-cyano-ethane
1-(4-trans-propylcyclohexyl)-2-(4-butoxyphenyl)-1-fluoro-ethane
1-(4-trans-propylcyclohexyl)-2-(4-butoxyphenyl)-1-chloro-ethane
1-(4-trans-propylcyclohexyl)-2-(4-butoxyphenyl)-1-bromo-ethane
1-(4-trans-propylcyclohexyl)-2-(4-butoxyphenyl)-1-cyano-ethane
1-(4-trans-propylcyclohexyl)-2-(4-(4-trans-pentylcyclohexyl)-phenyl)-1-fluoro-ethane
1-(4-trans-propylcyclohexyl)-2-(4-(4-trans-pentylcyclohexyl)-phenyl)-1-chloro-ethane
1-(4-trans-propylcyclohexyl)-2-(4-(4-trans-pentylcyclohexyl)-phenyl-1-bromo-ethane
1-(4-trans-propylcyclohexyl)-2-(4-(4-tans-pentylcyclohexyl)-phenyl)-1-cyano-ethane
1-(4-trans-propylcyclohexyl)-2-(4-(4-trans-pentylcyclohex-1-yl-methoxy)-phenyl)-1-fluoro-ethane
1-(4-trans-propylcyclohexyl)-2-(4-(4-trans-pentylcyclohex-1-yl-methoxy)-phenyl)-1-chloro-ethane
1-(4-trans-propylcyclohexyl)-2-(4-(4-trans-pentylcyclohex-1-yl-methoxy)-phenyl)-1-bromo-ethane
1-(4-trans-propylcyclohexyl)-2-(4-(4-trans-pentylcyclohex-1-yl-methoxy)-phenyl)-1-cyano-ethane
1-(4-trans-propylcyclohexyl)-2-(4-trans-(4-pentylphenyl)-cyclohexyl)-1-fluoro-ethane
1-(4-trans-propylcyclohexyl)o-2-(4-trans-(4-pentylphenyl)-cyclohexyl)-1-chloro-ethane
1-(4-trans-propylcyclohexyl)-2-(4-trans-(4-pentryl-phenyl)-cyclohexyl)-1-bromo-ethane
1-(4-trans-propylcyclohexyl)-2-(4-trans-(4-pentyl-phenyl)-cyclohexyl)-1-cyano-ethane
1-(4-trans-propylcyclohexyl)-2-(4-trans-(4-butoxy-phenyl)-cyclohexyl)-1-fluoro-ethane
1-(4-trans-propylcyclohexyl)-2-(4-trans-(4-butoxyphenyl-cyclohexyl)-1-chloro-ethane
1-(4-trans-propylcyclohexyl)-2-(4-trans-(4-butoxy-phenyl)-cyclophexyl)-1-bromo-ethane
1-(4-trans-propylcyclohexyl)-2-(4-trans-(4-butoxy-phenyl)-cyclohexyl)-1-cyano-ethane
1-(4-trans-propylcyclohexyl)-2-(4-trans-(4-pentyl-phenoxymethyl)-cyclohexyl)-1-fluoro-ethane
1-(4-trans-propylcyclohexyl)-2-(4-trans-(4-pentyl-phenoxymethyl)-cyclohexyl)-1-chloro-ethane
1-(4-trans-propylcyclohexyl)-2-(4-trans-(4-pentyl-phenoxymethyl)cyclohexyl)-1-bromo-ethane
1-(4-trans-propylcyclohexyl)-2-(4-trans-(4-pentyl-phenoxymethyl)-cyclohexyl)-1-cyano-ethane
1-(4-trans-propylcyclohexyl)-2-(4-trans-(4-butoxy-phenoxymethyl)-cyclohexyl)-1-fluoro-ethane
1-(4-trans-propylcyclohexyl)-2-(4-trans-(4-butoxy-phenoxymethyl)-cyclohexyl)-1-chloro-ethane
1-(4-trans-propylcyclohexyl)-2-(4-trans-(4-butoxy-phenoxymethyl)-cyclohexyl)-1-bromo-ethane
1-(4-trans-propylcyclohexyl)-2-(4-trans-(4-butoxy-phenoxymethyl)-cyclohexyl)-1-cyano-ethane 1-(4-propyl-1-bicyclo-(2,2,2)-octyl)-2-(4-trans-(4-pentyl-phenyl)-cyclohexyl)-1-fluoro-ethane
1-(4-propyl-1-bicyclo-(2,2,2)-octyl)-2-(4-trans-(4-pentylphenyl)-cyclohexyl)-1-chloro-ethane
1-(4-propyl-1-bicyclo-(2,2,2)-octyl)-2-(4-trans-(4-pentylphenyl)-cyclohexyl)-1-bromo-ethane
1-(4-propyl-1-bicyclo-(2,2,2)-octyl)-2-(4-trans-(4-pentylphenyl) -cyclohexyl)-1-cyano-ethane 1-(4-propyl-1-bicyclo-(2,2,2)-octyl)-2-(4-trans-(4-butoxyphenyl)-cyclohexyl)-1-fluoro-ethane
1-(4-propyl-1-bicyclo-(2,2,2)-octyl)-2-(4-trans-(4-butoxyphenyl)-cyclohexyl)-1-chloro-ethane
1-(4-propyl-1-bicyclo-(2,2,2)-octyl)-2-(4-trans-(4-butoxyphenyl)-cyclohexyl)-1-bromo-ethane
1-(4-propyl-1-bicyclo-(2,2,2)-octyl)-2-(4-trans-(4-butoxyphenyl)-cyclohexyl)-1-cyano-ethane
1-(4-propyl-1-bicyclo-(2,2,2)-octyl)-2-(4-(4-trans-pentylcyclohexyl)-phenyl-1-fluoro-ethane
1-(4-propyl-1-bicyclo-(2,2,2)-octyl)-2-(4-(4-trans-pentylcyclohexyl)-phenyl-1-chloro-ethane
1-(4-propyl-1-bicyclo-(2,2,2)-octyl)-2-(4-(4-trans-pentylcyclohexyl)-phenyl-1-bromo-ethane
1-(4-propyl-1-bicyclo-(2,2,2)-octyl)-2-(4-(4-trans-pentylcyclohexyl)-phenyl-1-cyano-ethane
1-(4-propyl-1-bicyclo-(2,2,2)-octyl)-2-(4-(4-trans-propyloxycarbonylcyclohexyl)-phenyl)-1-fluoro-ethane
1-(4-propyl-1-bicyclo-(2,2,2)-octyl)-2-(4-(4-trans-propyloxycarbonylcyclohexyl)-phenyl)-1-chloro-ethane
1-(4-propyl-1-bicyclo-(2,2,2)-octyl)-2-(4-(4-trans-propyloxycarbonylcyclohexyl)-phenyl)-1-bromo-ethane
1-(4-propyl-1-bicyclo-(2,2,2)-octyl)-2-(4-(4-trans-propyloxycarbonylcyclohexyl)-phenyl)-1-cyano-ethane
1-(4-trans-propyl-cyclohexyl)-2-(6-pentylpyridazin-3-yl)-1-fluoro-ethane
1-(4-trans-propyl-cyclohexyl)-2-(6-pentylpyridazin-3-yl)-1-chloro-ethane
1-(4-trans-propyl-cyclohexyl)-2-(6-pentylpyridazin-3-yl)-1-bromo-ethane
1-(4-trans-propyl-cyclohexyl)-2-(6-pentylpyridazin-3-yl)-1-cyano-ethane
1-(4-trans-propylcyclohexyl)-2-(6-butoxypyridazin-3-yl)-1-fluoro-ethane
1-(4-trans-propylcyclohexyl)-2-(6-butoxypyridazin-3-yl)-1-chloro-ethane
1-(4-trans-propylcyclohexyl)-2-(6-butoxypyridazin-3-yl)-1-bromo-ethane
1-(4-trans-propylcyclohexyl)-2-(6-butoxypyridazin-3-yl)-1-cyano-ethane
1-(4-trans-propylcyclohexyl)-2-(4-trans-(6-pentyl-pyridazin-3-yl)-cyclohexyl)-1-fluoro-ethane
1-(4-trans-propylcyclohexyl)-2-(4-trans-(6-pentyl-pyridazin-3-yl)-cyclohexyl)-1-chloro-ethane
1-(4-trans-propylcyclohexyl)-2-(4-trans-(6-pentyl-pyridazin-3-yl)-cyclohexyl)-1-bromo-ethane
1-(4-trans-propylcyclohexyl)-2-(4-trans-(6-pentyl-pyridazin-3-yl)-cyclohexyl)-1-cyano-ethane
1-(4-trans-propylcyclohexyl)-2-(4-trans-(6-butoxypyridazin-3-yl)-cyclohexyl)-1-fluoro-ethane
1-(4-trans-propylcyclohexyl)-2-(4-trans-(6-butoxypyridazin-3-yl)-cyclohexyl-1-chloro-ethane
1-(4-trans-propylcyclohexyl)-2-(4-trans-(6-butoxypyridazin-3-yl)-cyclohexyl-1-bromo-ethane
1-(4-trans-propylcyclohexyl)-2-(4-trans-(6-butoxypyridazin-3-yl)-cyclohexyl)-1-cyano-ethane
1-(4-trans-propylcyclohexyl)-2-(4-trans-(2-(6-pentylpyridazin-3-yl -ethyl)-cyclohexyl)-1-fluoro-ethane
1-(4-trans-propylcyclohexyl)-2-(4-trans-(2-(6-pentylpyridazin-3-yl)-ethyl)-cyclohexyl)-1-chloro-ethane
1-(4-trans-propylcyclohexyl)-2-(4-trans-(2-(6-pentylpyridazin-3-yl)-ethyl)-cyclohexyl)-1-bromo-ethane
1-(4-trans-propylcyclohexyl)-2-(4-trans-(2-(6-pentylpyridazin-3-yl)-ethyl)-cyclohexyl)-1-cyano-ethane
1-(4-trans-propylcyclohexyl)-2-(4-trans-(2-(6-butoxypyridazin-3-yl)-ethyl)-cyclohexyl)-1-fluoro-ethane
1-(4-trans-propylcyclohexyl)-2-(4-trans-(2-(6-butoxypyridazin-3-yl)-ethyl)-cyclohexyl)-1-bromo-ethane
1-(4-trans-propylcyclohexyl)-2-(4-trans-(2-(6-butoxypyridazin-3-yl)-ethyl)-cyclohexyl)-1-chloro-ethane
1-(4-trans-propylcyclohexyl)-2-(4-trans-(2-(6-butoxypyridazin-3-yl)-ethyl)-cyclohexyl)-1-cyano-ethane
1-(4-trans-propylcyclohexyl)-2-(6-(4-trans-pentylcyclohexyl)-pyridazin-3-yl)-1-fluoro-ethane
1-(4-trans-propylcyclohexyl)-2-(6-(4-trans-pentylcyclohexyl)-pyridazin-3-yl)-1-chloro-ethane
1-(4-trans-propylcyclohexyl)-2-(6-(4-trans-pentylcyclohexyl)-pyridazin-3-yl)-1-bromo-ethane
1-(4-trans-propylcyclohexyl)-2-(6-(4-trans-pentylcyclohexyl)-pyridazin-3-yl)-1-cyano-ethane
1-(4-trans-propylcyclohexyl)-2-(6-(2-(4-trans-pentylcyclohexyl)-ethyl)-pyridazin-3-yl)-1-fluoro-ethane
1-(4-trans-propylcyclohexyl)-2-(6-(2-(4-trans-pentylcyclohexyl)-ethyl)-pyridazin-3-yl)-1-chloro-ethane
1-(4-trans-propylcyclohexyl)-2-(6-(2-(4-trans-pentylcyclohexyl)-ethyl)-pyridazin-3-yl)-1-bromo-ethane
1-(4-trans-propylcyclohexyl)-2-(6-(2-(4-trans-pentylcyclohexyl)-ethyl)-pyridazin-3-yl)-cyano-ethane
1,2-bis-(4-trans-cyanomethylcyclohexyl)-1-fluoro-ethane
1,2-bis-(4-trans-cyanopropylcyclohexyl)-1-fluoro-ethane
1-(4'-trans-fluoropropyl-4-trans-bicyclohexyl)-2-(4-trans-fluoropropylcyclohexyl)-2-chloro-ethane
1-(4'-trans-fluoropropyl-4-trans-bicyclohexyl)-2-(4-trans-fluoropropylcyclohexyl)-2-cyano-ethane
1-(4'-trans-fluoropropyl-4-trans-bicyclohexyl)-2-(4-trans-fluoropropyloxycarbonylcyclohexyl)-2-chloroethane
1-(4'-trans-fluoropropyl-4-trans-bicyclohexyl)-2-(4-trans-fluoropropyloxycarbonylcyclohexyl)-2-cyano-ethane
1-(4-trans-(2-(4-trans-cyanopropylcyclohexyl)-ethyl)-cyclohexyl) -2-(4-trans-propylcyclohexyl)-2-fluoro-ethane
1-(4-trans-(2-(4-trans-fluoropropylcyclohexyl)-ethyl)-cyclohexyl)-2-(4-trans-propylcyclohexyl)-2-fluoro-ethane
1-(4-trans-(2-(4-trans-chloropropylcyclohexyl)-ethyl)-cyclohexyl)-2-(4-trans-propylcyclohexyl)-2-chloro-ethane
1-(4-trans-(2-(4-trans-cyanopropylcyclohexyl)-ethyl)-cyclohexyl)-2-(4-trans-propylcyclohexyl)-2-cyano-ethane
1-(4-trans-cyanopropylcyclohexyl)-2-(4-pentylphenyl)-1-fluoro-ethane
1-(4-trans-fluoropropylcyclohexyl)-2-(4-pentylphenyl)-1-fluoro-ethane
1-(4-trans-chloropropylcyclohexyl)-2-(4-pentylphenyl)-1-chloro-ethane
1-(4-trans-cyanopropylcyclohexyl)-2-(4-pentylphenyl)-1-cyano-ethane
1-(4-trans-cyanopropylcyclohexyl)-2-(4-butoxyphenyl)-1-fluoro-ethane
1-(4-trans-fluoropropylcyclohexyl)-2-(4-butoxyphenyl)-1-fluoro-ethane.
1,2-bis-(4-trans-heptylcyclohexyl)-1-cyanoethane
1,2-bis-(4-trans-hexylcyclohexyl)-1-cyanoethane
1,2-bis-(4-trans-butylcyclohexyl)-1-cyanoethane
1,2-bis-(4-trans-propylcyclohexyl)-1-cyanoethane
1-(4-trans-propylcyclohexyl)-2-(4-trans-butylcyclohexyl)-1-cyanoethane 1-(4-trans-propylcyclohexyl)-2-(4-trans-pentylcyclohexyl)-1-cyanoethane
1-(4-trans-propylcyclohexyl)-2-(4-trans-hexylcyclohexyl)-1-cyanoethane
1-(4-trans-propylcyclohexyl)-2-(4-trans-heptylcyclohexyl)-1-cyanoethane
1-(4-trans-butylcyclohexyl)-2-(4-trans-pentylcyclohexyl)-1-cyanoethane
1-(4-trans-butylcyclohexyl)-2-(4-trans-hexylcyclohexyl)-1-cyanoethane
1-(4-trans-butylcyclohexyl)-2-(4-trans-heptylcyclohexyl)-1-cyanoethane
1-(4-trans-pentylcyclohexyl)-2-(4-trans-hexylcyclohexyl)-1-cyanoethane
1-(4-trans-pentylcyclohexyl)-2-(4-trans-heptylcyclohexyl)-1-cyanoethane
1-(4-trans-hexylcyclohexyl)-2-(4-trans-heptylcyclohexyl)-1-cyanoethane The following examples relate to liquid crystal mixtures according to the invention comprising at least one component of the formula (1):

EXAMPLE A

A liquid crystal mixture consisting of

| | |
|---|---|
| 11% by weight | trans,trans-4-propyl-4'-methoxycyclohexylcyclohexane, |
| 10% by weight | trans,trans-4-propyl-4'-ethoxycyclohexylcyclohexane, |
| 4% by weight | trans,trans-4-propylcyclohexylcyclohexane-4'-carboxylic acid-trans-4-propylcyclohexylester, |
| 4% by weight | trans,trans-4-propylcyclohexylcyclohexane-4'-carboxylic acid-trans-4-pentylcyclohexylester, |
| 4% by weight | trans,trans-4-butylcyclohexylcyclohexane-4'-carboxylic acid-trans-4-propylcyclohexylester, |
| 4% by weight | trans-trans-4-butylcyclohexylcyclohexane-4'-carboxylic acid-trans-4-pentylcyclohexylester, |
| 34% by weight | 1-(4-trans-buty cyclohexy)-2-(4-trans-heptylcyclohexyl)-1-cyanoethane and |
| 29% by weight | 1,2-bis-(4-trans-pentylcyclohexyl)-1-cyanoethane | has a negative DCA.

EXAMPLE B

A liquid crystal mixture consisting of

| | |
|---|---|
| 20% by weight | 1,2-bis-(4-trans-propylcyclohexyl)-1-cyanoethane |
| 21% by weight | 1,2-bis-(4-trans-pentylcyclohexyl)-1-cyanoethane |
| 22% by weight | 1-(4'-trans-pentyl-4-trans-bicyclohexy)-2-(4-trans-pentylcyclohexyl)-2-cyanoethane, |
| 11% by weight | trans,trans-4-propyl-4'-methoxycyclohexylcyclohexane |
| 10% by weight | trans,trans-4-propyl-4'-ethoxycyclohexylcyclohexane |
| 4% by weight | trans,trans-4-propylcyclohexylcyclohexane-4'-carboxylic acid-trans-4-propylcyclohexylester, |
| 4% by weight | trans-trans-4-propylcyclohexylcyclohexane-4'-carboxylic acid-trans-4-pentylcyclohexylester, |
| 4% by weight | trans,trans-4-butylcyclohexylcyclohexane-4'-carboxylic acid-trans-4-propylcyclohexylester , |
| 4% by weight | trans,trans-4-butylcyclohexylcylohexane-4'-carboxylic acid-trans-4-pentylcyclohexylester, | has a negative DCA.

EXAMPLE C

A liquid crystal mixture consisting of

| | |
|---|---|
| 30% by weight | 1-(4-trans-butylcyclohexyl)-2-(4-trans-heptylcyclohexyl)-1-cyanoethane, |
| 16% by weight | trans,trans-4-propyl-4'-methoxycyohexylcyclohexane |
| 15% by weight | trans,trans-4-propyl-4'-ethoxycyclohexylcyclohexane, |
| 4% by weight | trans,trans-4-propylcyclohexylcyclohexane-4'-carboxylic acid-trans-4-propylcyclohexylester, |
| 4% by weight | trans,trans-4-propylcyclohexylcyclohexane-4'-carboxylic acid-trans-4-pentylcyclohexylester, |
| 4% by weight | trans,trans-4-butylcyclohexylcyclohexane-4'-carboxylic acid-trans-4-propylcyohexylester |
| 4% by weight | trans,trans-4-butylcyclohexylcyclohexane-4'-carboxylic acid-trans-4-pentylcyclohexylester |
| 8% by weight | trans-4-propylcyclohexane-carboxylic acid-(trans-4-propylcyclohexylester), |
| 7% by weight | trans-4-pentylcyclohexane-carboxylic acid-(trans-4-pentycyclohexylester) and |
| 8% by weight | trans-4-hexylcyclohexane carboxylic acid-(trans-4-heptylcyclohexylester) | has a negative DCA.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

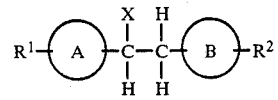

wherein x is cyano or halo,
A is a cycloaliphatic radical of the formula (1a) or (1b)

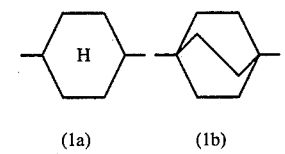

(1a)    (1b)

B is a cycloaliphatic radical of the formula (1a) or (1b) or an aromatic radical of the formula (1c) or (1d)

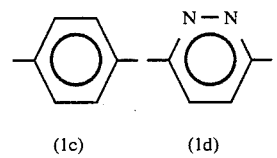

(1c)    (1d)

$R^1$ and $R^2$ are identical or different and each is a radical of the formula (1e)

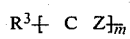 (1e)

C has one of the meanings given for ring B, $R^3$ is hydrogen, alkyl, alkoxy, alkoxy-carbonyl or alkyl-carbonyloxy wherein the alkyl portion of each contains 1-12 C atoms, or such a $C_{1-12}$-group which carries one or more substituents which are halo or cyano, at most one of these substituents being attached to each atom of the carbon chain, Z is a covalent bond or a bridge group of the formula $-CH_2O-$, $-OCH_2-$, $-C(X^1)(H)-CH_2-$, $-CH_2-C(X^1)(H)-$, $-OOC-$ or $-COO-$, $X^1$ is hydrogen or has one of the meanings given for X, and m is 0 or 1, with the provisos that
(a) groups of the formula $-CH_2O-$ or $-C(X)(H)-$ are not bonded directly via their C atoms to any aromatic radical of the formula (1c) or (1d) present in the molecule, except when X=F, and
(b) $R^3$ is not hydrogen if m is 0 or if C is cycloaliphatic.

2. A compound of claim 1, wherein in formula (1), X is cyano.

3. A compound of claim 1, wherein formula (1) contains a total of two, three or four cycloaliphatic radicals of the formula (1a).

4. A compound of claim 1, wherein the alkyl portion of $R^3$ contains 3-9 C atoms.

5. A compound of claim 1 having formula (2)

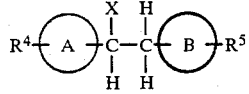 (2)

wherein X, A and B are as defined in claim 1 and $R^4$ and $R^5$ are identical or different and have one of the meanings given for $R^3$, with the exception of hydrogen.

6. A compound of claim 1, having the formula (3)

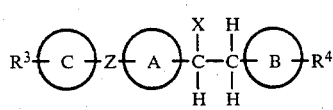 (3)

wherein X, A, B, C, Z and $R^3$ are as defined in claim 1 and $R^4$ has one of the meanings given for $R^3$.

7. A compound of claim 1, having the formula (4)

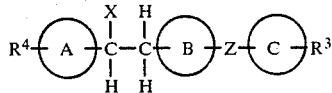 (4)

wherein X, A, B, C, Z and $R^3$ are as defined in claim 1 and $R^4$ has one of the meanings given for $R^3$.

8. A compound of claim 5, wherein X is cyano.
9. A compound of claim 6, wherein X is cyano.
10. A compound of claim 7, wherein X is cyano.
11. A compound of claim 1, having the formula (5)

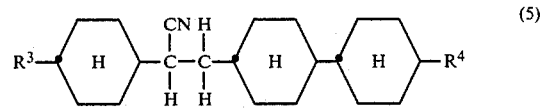 (5)

wherein $R^4$ has one of the meanings given for $R^3$ in claim 1, and $R^3$ and $R^4$ are identical or different but are not hydrogen.

12. A compound of claim 11, wherein $R^3$ and $R^4$ are each a $C_1$-$C_{12}$-alkyl radical.

13. A compound of claim 12, wherein at least one of $R^3$ and $R^4$ is n-pentyl.

14. A compound of claim 1, wherein the alkyl portions are straight chained.

15. A compound of claim 1, having the formula (6)

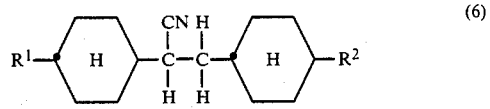 (6)

wherein $R^1$ and $R^2$ are as defined in claim 1.

16. A compound of claim 15, wherein $R^1$ is a $C_1$-$C_{12}$—alkyl radical and $R^2$ is $R^3$

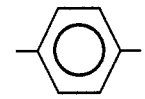

17. A compound of claim 1, having the formula (7)

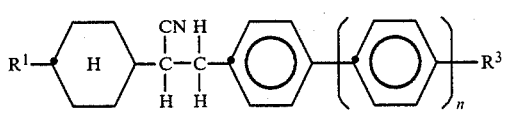 (7)

wherein $R^1$ and $R^3$ are as defined in claim 1 and n is 0 or 1.

* * * * *